United States Patent [19]

Portoghese

[11] Patent Number: 4,816,586
[45] Date of Patent: Mar. 28, 1989

[54] DELTA OPIOID RECEPTOR ANTAGONISTS

[75] Inventor: Philip S. Portoghese, Falcon Heights, Minn.

[73] Assignee: Regents of the University of Minnesota, Minneapolis, Minn.

[21] Appl. No.: 79,216

[22] Filed: Jul. 29, 1987

[51] Int. Cl.⁴ .................... C07D 489/00; C07D 489/06
[52] U.S. Cl. ..................................... 544/340; 544/339; 544/341; 546/31; 546/34
[58] Field of Search ............... 546/31, 34; 544/338, 544/339, 341

[56] References Cited

U.S. PATENT DOCUMENTS 4,649,200 3/1987 Portoghese et al. ................. 546/26

OTHER PUBLICATIONS

Y. Sawa et al., Chem. Abstracts, 73, 398, 120798v (1970).
C. F. C. Smith et al., Life Sci., 40, 267 (1987).

Primary Examiner—Donald G. Daus
Assistant Examiner—Diana G. Rivers
Attorney, Agent, or Firm—Merchant, Gould, Smith, Edell, Welter & Schmidt

[57] ABSTRACT

Delta-opioid receptor antagonists are disclosed of the formula:

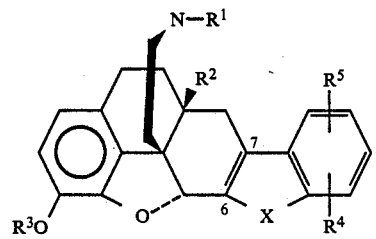

OR

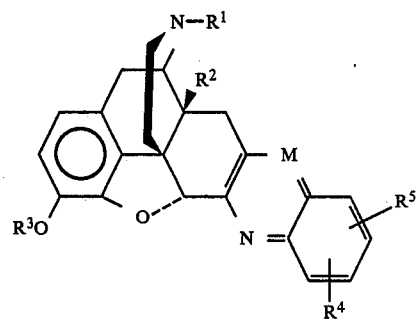

wherein $R^1$ is $(C_1-C_5)$alkyl, $C_3-C_6$(cycloalkyl)alkyl, $C_5-C_7$(cycloalkenyl)alkyl, aryl, aralkyl, trans-$(C_4-C_5)$alkenyl, allyl or furan-2-ylalkyl, $R^2$ is H, OH or $O_2CR$, wherein R is $(C_1-C_5)$alkyl; $R^3$ is H, $(C_1-C_5)$alkyl or RCO; X is O, S or NY, wherein Y is H or $(C_1-C_5)$alkyl; M is N or CH; and $R^4$ and $R^5$ are individually H, F, Cl, Br, $NO_2$, $NH_2$, $(C_1-C_5)$alkyl or $(C_1-C_5)$alkoxy or $R^4$ and $R^5$ together are benzo; and the pharmaceutically acceptable salts thereof.

25 Claims, 1 Drawing Sheet

DELTA OPIOID RECEPTOR ANTAGONISTS

This invention was made with Government support under Grant No. 5ROI-DA 0153311, awarded by the National Institute on Drug Abuse. The Government has certain rights in the invention.

BACKGROUND OF THE INVENTION

Endogenous opioid peptides are involved in the mediation or modulation of a variety of physiological processes, many of which are mimicked by opiates or other non-endogenous opioid ligands. Some of the effects that have been investigated are analgesia, tolerance and dependence, appetite, renal function, gastrointestinal motility, gastric secretion, learning and memory, mental illness, epileptic seizures and other neurologic disorders, cardiovascular responses, and respiratory depression.

The fact that the effects of endogenous and exogeneous opioids are mediated by at least three different type [mu ($\mu$), delta ($\delta$), kappa ($\kappa$)] of opioid receptors raises the possibility that highly selective exogenous opioid agonist or antagonist ligands might have therapeutic applications. See W. R. Martin, *Pharmacol. Rev.*, 35, 283 (1983). Thus, if a ligand acts at a single opioid receptor type or subtype, the potential side-effects mediated through other opioid receptor types will be minimized or eliminated. The prototypical opioid antagonists, naloxone and naltrexone, are used primarily as pharmacologic research tools and for the reversal of toxic effects of opioids in cases of overdose. However, since these antagonists act at multiple opioid receptors, their application in other therapeutic areas or as pharmacologic tools appear to be limited.

Some progress has been made in the development of highly selective opioid antagonists. For example, Portoghese et al. (U.S. Pat. No. 4,649,200) disclose certain bimorphinans which possess high selectivity and potency at kappa opioid receptors. Minimal involvement was observed at mu and delta opioid receptors. Pentapeptides related to the enkephalins have been reported to be highly delta-selective opioid antagonists. Such compounds (e.g., ICI 174864) currently are employed as pharmacologic tools, but they possess the disadvantage of low potency and poor penetration into the central nervous system (CNS). See J. W. Shaw et al., *Life Sci.*, 31, 1259 (1982) and R. Cotton et al., *Eur. J. Pharmacol.*, 97, 331 (1984).

Therefore, a need exists for new compounds that are both highly selective and potent as delta opioid antagonists. A further need for delta opioid antagonists exists which exhibit an access into the CNS which is superior to the known peptide delta antagonists.

BRIEF DESCRIPTION OF THE INVENTION

The present invention is directed to biologically-active compounds of the formula I:

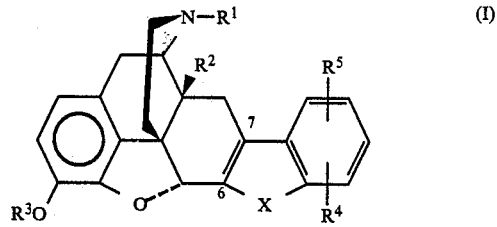

wherein $R^1$ is $(C_1-C_5)$alkyl, $C_3$-$C_6$(cycloalkyl)alkyl, $C_5$-$C_7$(cycloalkenyl)alkyl, aryl, aralkyl, trans-$(C_4-C_5)$alkenyl, allyl or furan-2-ylalkyl, $R^2$ is H, OH or $O_2C(C_1-C_5)$alkyl; $R^3$ is H, $(C_1-C_5)$alkyl or $((C_1-C_5)$alkyl)-C=O; X is O, S or NY, wherein Y is H or $(C_1-C_5)$alkyl; and $R^4$ and $R^5$ are individually H, F, Cl, Br, $NO_2$, $NH_2$, $(C_1-C_5)$alkyl, $(C_1-C_5)$alkoxy or together are benzo; and the pharmaceutically-acceptable salts thereof.

The present invention is also directed to biologically active compounds of formula II:

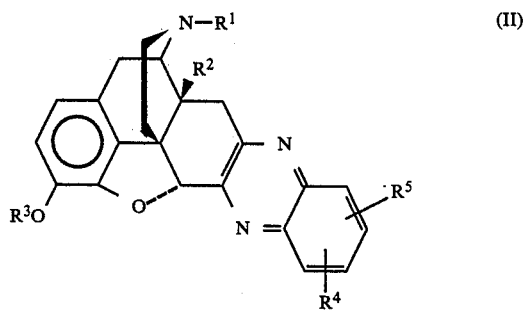

wherein $R^1$ is $(C_1-C_5)$alkyl, $C_3-C_6$(cycloalkyl)alkyl, $C_5-C_7$(cycloalkenyl)alkyl, aryl, aralkyl, trans-$(C_4-C_5)$alkenyl, allyl or furan-2-ylalkyl, $R^2$ is H, OH or $O_2C(C_1-C_5)$alkyl; $R^3$ is H, $(C_1-C_5)$alkyl or $((C_1-C_5)$alkyl)-C=O; M is N or CH, and $R^4$ and $R^5$ are as described for formula I hereinabove; and the pharmaceutically-acceptable salts thereof.

The alkyl moiety present in the $R^1$ group which links the cycloalkyl, cycloalkenyl, aryl, or furan-2-yl moiety to the basic nitrogen atom is a lower(alkyl) group, preferably $-(CH_2)_n-$, wherein n is about 1-5, most preferably n is 1, e.g., $R^1$ is $C_3-C_6$(cycloalkyl)methyl, $C_5-C_7$(cycloalkenyl)methyl, arylmethyl or furan-2-ylmethyl. Preferred aryl moieties include phenyl, benzyl, tolyl, xylyl, anisyl and the like.

In formulas I or II, the position of the $-R^4$ and $-R^5$ groups indicate that they can be either ortho, meta or para to the $-X$ group or the $-N=$group, respectively, e.g., $R^4$ and/or $R^5$ can occupy any available site on the phenyl ring. In structures I and II, a bond designated by a wedged or darkened line indicates one extending above the plane of the phenyl rings. A bond designated by a broken line indicates one extending below the plane of the phenyl rings.

These delta-opioid antagonists include compounds of the formula I or formula II wherein $R^1$ is $C_3-C_6$(cycloalkyl)alkyl or $C_5-C_7$(cycloalkenyl)alkyl, preferably wherein $R^1$ is $C_3-C_6$(cycloalkyl)methyl, and most preferably wherein $R^1$ is cyclopropylmethyl. Y can be H or $(C_1-C_5)$alkyl, preferably H, methyl or ethyl; $R^2$ is preferably OH or OAc ($O_2CCH_3$), and $R^3$ preferably is H. Preferably, at least one, and most preferably, both of $R^4$ and $R^5$ are H. Preferred compounds also result when $R^4$ is H and $R^5$ is F, ($C_1$-$C_5$)alkyl or ($C_1$-$C_5$)alkoxy.

For example, in one assay, indole I, where $R^1$ is cyclopropylmethyl, $R^2$ is OH, $R^3$ is H and $R^4$ is H, is at least 30 times more potent than the peptide delta antagonist, ICI 174864, and is more selective than the structurally unrelated opiate M8008. Since the compounds of the invention are formally morphinan derivatives, it is believed that their ability to cross the "blood-brain barrier" and to affect the CNS should be far superior to peptide delta opioid antagonists.

Therefore, the present invention is also directed to a method for blocking delta-opioid receptors in mammalian tissue comprising contacting said receptors with an effective amount of one of the present delta-opioid antagonists of formula I or formula II. These antagonists can be used as pharmacologic and biochemical probes of opioid receptor structure and function, and may also be useful clinically, e.g., to counteract life-threatening shock.

Furthermore, it is believed that other types of fused ring systems that can maintain a planar geometry similar to that of the indole (X=NH), benzo furan (X=O) or benzothiophene (X=S), moiety also should confer high delta receptor activity on compounds of formula I (e.g., indane (R=$CH_2$), napthalene and the like).

FIG. 1 is a schematic depiction of reaction sequences leading to compounds of the invention.

DETAILED DESCRIPTION OF THE INVENTION

Chemistry

Figure 1:
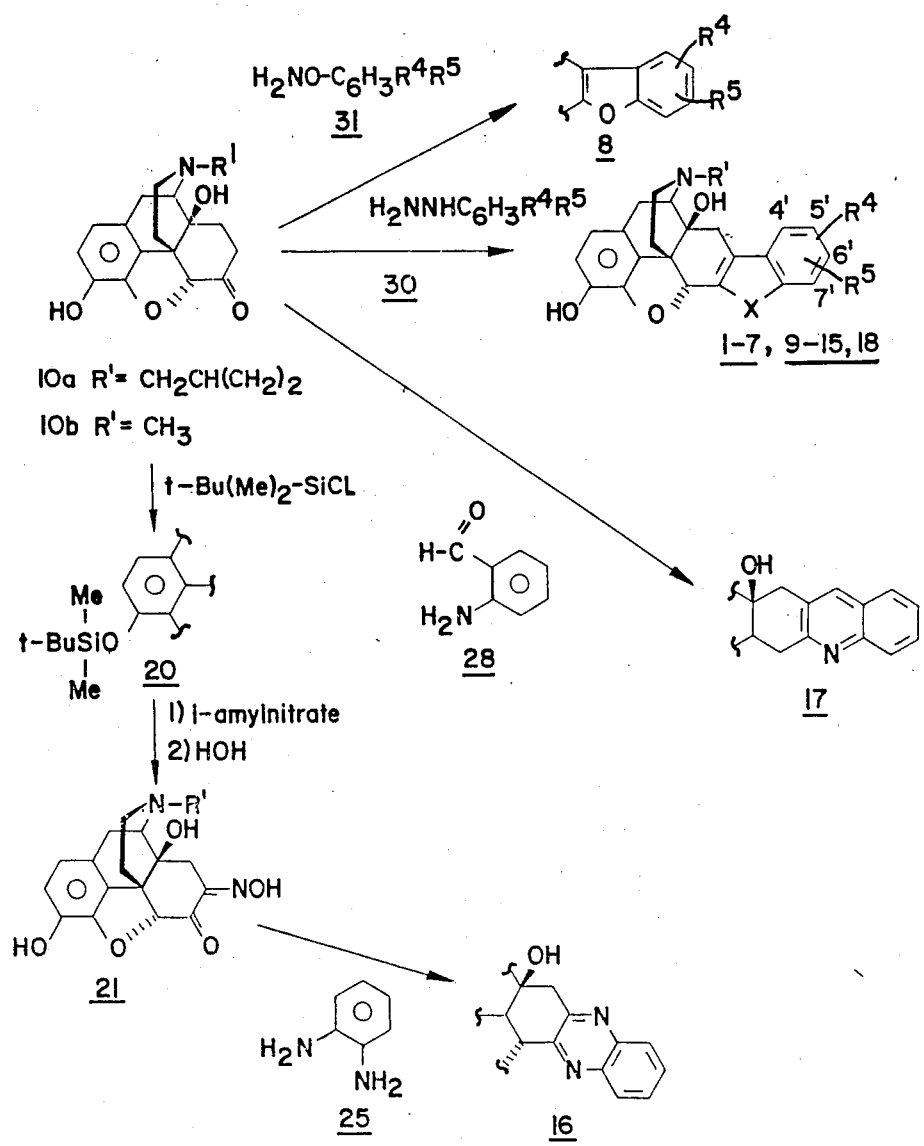

Representative compounds of formula I (1-15 and 18) or formula II (16-17) were synthesized from starting materials of formula 10a or 10b as outlined in FIG. 1. The structures of compounds 1-7, 9-15 and 18, shown generally in FIG. 1, are summarized on Table I, below.

TABLE I

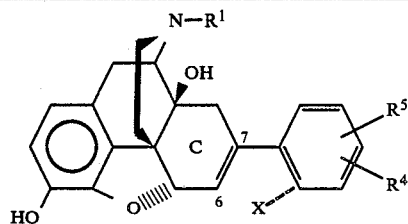

| Compound No. of Table I | $R^1$ | X | $R^4$ | $R^5$ |
|---|---|---|---|---|
| 1 | $CpCH_2$[1] | NH | H | H |
| 2 | $CpCH_2$ | $NCH_3$[2] | H | H |
| 3 | $CpCH_2$ | NH | H | 5'-F |
| 4 | $CpCH_2$ | NH | H | 5'-$OCH_3$ |
| 5 | $CpCH_2$ | NH | H | 5'-$CH_3$ |
| 6 | $CpCH_2$ | NH | H | 5'-$NO_2$ |
| 7 | $CH_3$ | NH | H | H |
| 9[3] | $CpCH_2$ | NH | H | 5'-OH |
| 10 | $CpCH_2$ | NH | H | 4'-F |
| 11 | $CpCH_2$ | NH | H | 7'-F |
| 12 | $CpCH_2$ | NH | H | 4' and 6'-$CH_3$ (mixture) |
| 13 | $CpCH_2$ | NH | H | 7'-$CH_3$ |
| 14 | $CpCH_2$ | NH | H | 7'-$OCH_3$ |
| 15[4] | $CpCH_2$ | NH | H | 7'-OH |

TABLE I-continued

| Compound No. of Table I | $R^1$ | X | $R^4$ | $R^5$ |
|---|---|---|---|---|
| 18 | $CpCH_2$ | NH | 6'-CH=CH—CH=CH—7' | |

[1]Cyclopropylmethyl.
[2]From Fischer indole synthesis of 10a + $H_2NN(CH_3)Ph$.
[3]Derived from 4 using 5 equivalents of $BBr_3$.
[4]Hydrolysis product formed during synthesis of 14.

Compounds 1-18 have either indole (1-7, 9-15), benzofuran (8), benzopyrazine (16), benzoquinoline (17) or benzoindole (18) moieties, fused to the 6,7-position of the opiate C-ring.

Starting Materials

The structures, common names and Merck Index reference numbers of representative 4,5-epoxy-6-ketomorphinan starting materials of general formula 10 are summarized on Table II, below.

TABLE II

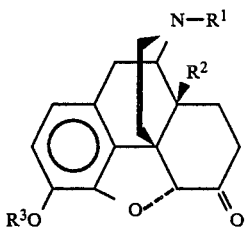

| Compound | $R^1$ | $R^2$ | $R^3$ | Common Name | Merck No.[2] |
|---|---|---|---|---|---|
| 10a | $CH_2CH(CH_2)_2$ | OH | H | naltrexone | 6209 |
| 10b | $CH_3$ | OH | H | oxymorphone | 6837 |
| 10c | $CH_3$ | H | H | hydromorphone | 4714 |
| 10d | $CH_3$ | H | $CH_3$ | hydrocodone | 4687 |
| 10e[1] | $CH_2CH(CH_2)_2$ | H | H | — | — |
| 10f | $CH_2CH=CH_2$ | OH | H | naloxone | 6208 |
| 10g | $CH_3$ | OH | $CH_3$ | oxycodone | 6827 |

[1]Preparation: M. Gates et al., J. Med. Chem., 7, 127 (1964).
[2]The Merck Index, W. Windholz, ed., Merck & Co., Rahway, NJ (10th ed. 1983).

Other starting materials of formula 10 can be prepared by synthetic methods which are well-known in the art of organic chemistry. For example, compounds of formula 10 wherein $R^1$ is H and $R^3$ is a suitable protecting group, and wherein the 6-keto group has also been protected, can be prepared from compounds 10a-g. These intermediates can be N-alkylated and deprotected to yield compounds of formula I wherein $R^1$ is $C_2$-$C_5$(alkyl), $C_4$-$C_6$(cycloalkyl)alkyl, $C_5$14 $C_7$(cycloalkenyl)alkyl, aryl, aralkyl, trans-$C_4$-$C_5$-alkenyl or furan-2-ylalkyl, by the application of well-known reactions.

For example, the free hydroxyl groups of compounds of formula 10, e.g., $R^2$=OH and/or $R^3$=H, can be protected by acid-labile groups such as tetrahydropyranl-yl, trimethylsilyl, 1-methoxy-isopropyl and the like as disclosed in *Compendium of Organic Synthetic Methods*, I. T. Harrison et al., eds., Wiley-Interscience, New York, NY (1971) at pages 124–131, (hereinafter "Compendium"), the disclosure of which is incorporated by reference herein. The protection of the 6-keto group of compounds of formula 10 by its reversible conversion into a ketal or a thioketal group is disclosed in *Compendium*, at pages 449–453, the disclosure of which is incorporated by reference herein. Methods for the demethylation of N-methyl amines have been disclosed, for example, in *Compendium* at page 247, *J. Amer. Chem. Soc.*, 89, 1942 (1967) and *J. Amer. Chem. Soc.*, 77, 4079 (1955), the disclosures of which are incorporated by reference herein.

Procedures for the alkylation of secondary amines with halides under basic or neutral conditions are well-known. For example, see *Compendium* at pages 242–245; *Org. Synth.*, 43, 45 (1963); *J. Org. Chem.*, 27, 3639 (1962) and *J. Amer. Chem. Soc.*, 82, 6163 (1960), the disclosures of which are incorporated by reference herein.

Compounds of formula I or II wherein $R^2$ is acyloxy and/or $R^3$ is acyl can be prepared by using the corresponding starting material 10. For example, starting material 10a can be diacylated by reacting it with the appropriate ($C_1$–$C_5$)alkyl anhydride in pyridine for 10–18 hrs at 18°–25° C. The resultant 3,14-diacylated compound can be converted to the 14-acylated compound by limited hydrolysis. The 3-acylated starting materials can be prepared by the short-term reaction of the compound of formula 10 with the anhydride, e.g., for about 2–4 hours. The 3-acylated product can be separated from the 3,14-diacylated product by chromatography.

SYNTHESIS OF DELTA OPIOID RECEPTOR ANTAGONIST

The preparation of 1–7, 9–15 and 18 was accomplished using the Fischer indole synthesis. See R. B. Van Orden et al., *Chem. Rev.*, 30, 78 (1942), the disclosure of which is incorporated by reference herein. A compound of formula 10, e.g., naltrexone hydrochloride (10a.HCl) or oxymorphone hydrochloride (10b.HCl) and the appropriate aromatic hydrazine hydrochloride (30) were refluxed in glacial acetic acid or methanol containing an organic or inorganic acid such as methanesulfonic acid or hydrochloric acid (HCl) for 3–6 hours. The 6',7'-benzo-derivative (18), was prepared by refluxing naltrexone.HCl with 1-napthylhydrazine.

Benzofuran 8 was prepared by refluxing an ethanol solution of 10a.HCl, methane sulfonic acid and o-phenylhydroxylamine.HCl (31).

The benzopyrazine 16 was synthesized from 10a.HCl by a conversion to the oximino derivative 21 followed by reaction with o-phenylenediamine 25.

The quinoline derivative 17 was prepared by refluxing naltrexone.HCl with o-aminobenzaldehyde 28 with methanesulfonic acid in ethanol. The corresponding benzothiophene derivatives (I, X=S) can be synthesized by reacting a compound of formula 10 with thiophenol in the presence of an acid, followed by photolysis of the OH-protected thioenol under a nitrogen atmosphere using a Hg high pressure lamp (see S. H. Green et al., *J. Org. Chem.*, 33, 2218 (1968), the disclosure of which is incorporated by reference herein).

The acid salts of compounds of formulas I or II wherein $R^3$=H can be converted into the corresponding ($C_1$–$C_5$)alkoxy derivatives [$R^3$=($C_1$–$C_5$)alkyl] by dissolving the starting material in DMF and adding an excess of the appropriate ($C_1$–$C_5$)alkyl iodide and an amine such as diisopropylethylamine. The reaction can be conducted at an elevated temperature for about 4–10 hours. The final product can be purified by column chromatography.

The invention also comprises the pharmaceutically-acceptable salts of the biologically-active compounds of formula I or II, together with a pharmaceutically-acceptable carrier for administration in effective, non-toxic dose form. Pharmaceutically-acceptable amine salts may be salts of organic acids, such as acetic, citric, lactic, malic, tartaric, p-toluene sulphonic acid, methane sulfonic acid, and the like as well as salts of pharmaceutically-acceptable mineral acids such as phosphoric, hydrochloric or sulfuric acid, and the like.

These physiologically-acceptable salts are prepared by methods known in the art, e.g., by dissolving the free amine bases with an excess of the acid in aqueous alcohol.

ADMINISTRATION

In clinical practice, the compounds of the present invention will normally be administered orally or parenterally, as by injection or infusion, in the form of a pharmaceutical preparation comprising the active ingredient in combination with a pharmaceutically-acceptable carrier which may be a solid, semi-solid or liquid diluent or an ingestible capsule. The compound or its salt may also be used without carrier material. As examples of pharmaceutical carriers may be mentioned tablets, intravenous solutions, suspensions, liposomes and the like. Usually, the active substance will comprise between about 0.05 and 99%, or between 0.1 and 95% by weight of the resulting preparation, for example, between about 0.5 and 20% of preparation intended for injection or infusion and between 0.1 and 50% of preparations intended for oral administration.

The invention will be further described by reference to the following detailed examples, wherein melting points were determined with a Thomas-Hoover melting point apparatus and are uncorrected. Elemental analyses were done by MHW Laboratories. IR spectra were determined on a Perkin Elmer 281 Infrared spectrophotometer, UV were recorded on a Beckman DU-8 spectrophotometer, NMR data were obtained on a JOEL 360 MHz using $Me_4Si$ as internal standard and mass spectra were obtained on a Finnigan 4000 or AEI MS-30. Physical properties of 1–17 are listed in Table III, hereinbelow.

EXAMPLE I

17-Cyclopropylmethyl-6,7-dehydro-4,5α-epoxy-3,14-dihydroxy-6,7,2',3'-indolomorphinan (1)

A mixture of naltrexone.HCl (10a.HCl) (1.5 g, 4 mmol) and phenylhydrazine.HCl (1.16 g, 8 mmol) were refluxed in 50 ml of HCl-saturated methanol for 4 hours. The mixture then was cooled, diluted with water (10 ml) and extracted with chloroform. The aqueous phase was basified with sodium bicarbonate and extracted with ethyl acetate (3×50 ml). The solvent was removed in vacuo and the solid residue (1.5 g) was chromatographed on a deactivated silica gel column (150 g, 60–200 mesh, 97:3:1 of $CHCl_3$/MeOH/$NH_4OH$) to afford 1.2 g (71%) of 1: λ max 225,282; EIMS m/e 414 (M+, 100%). The base was converted to the hydrochloride salt which was crystallized from EtOH-$CHCl_3$, mp 270° C. (decomp).

EXAMPLE II

The synthesis of compounds 3–6, 10–14 and 18 is generally accomplished as described in Example I, hereinabove, with the exception that 4-fluoro-, 4-methoxy-, 4-methyl-, 4-nitro-, 3-fluoro-, 2-fluoro-, 3,4-dimethyl-, 2-methyl-, 2'-methoxy-(phenylhydrazine). HCl, and 1-naphthylhydrazine, respectively, were substituted for the phenylhydrazine.HCl used in Example I. Variations in the acidic solvent are noted on Table III, below.

EXAMPLE III

The synthesis of compound 7 is accomplished as described in Example I, above, but substituting oxymorphone for naltrexone.

EXAMPLE IV 6,7,2',3'-Benzofurano-17-cyclopropylmethyl-6,7-dehydro-3,14-dihydroxy-4,5α-epoxymorphinan (8)

A mixture of naltrexone.HCl (10.HCl)(0.38 g, 1 mmol), O-phenylhydroxylamine.HCl (0.30 g, 2 mmol) and methanesulfonic acid (0.3 g, 0.3 mmol) were refluxed in ethanol (20 ml) for 18 hours. The volume of the reaction mixture was then reduced in vacuo and the crystalline methanesulfonate salt (8.CH$_3$SO$_3$H), mp 250° C. (decomp), that formed on standing was separated from the mother liquor by filtration. Yield, 0.88 g (80%). EIMS m/e 415 (M+).

EXAMPLE V 6,7,2',3'-benzopyrazino-17-cyclopropylmethyl-6,7-dehydro-3,14-dihydroxy-4,5α-epoxymorphinan (16)

A. t-Butyldimethylsilyl ether (20)

To a stirred solution of 2 g of naltrexone hydrochloride (5.3 mmole) in 6 ml of DMF were added 2 g of imidazole (29.4 mmole) and 2 g of t-butyldimethylsilyl chloride (13.2 mmole). The solution was stirred at room temperature for 40 min. To the mixture was added ether and water. The resulting mixture was extracted with ether three times. The combined ether layers were washed with brine, dried over sodium sulfate and potassium carbonate (1:1) and concentrated to give crude 20, which was recrystallized from ethanol to afford 2.12 g of 20, mp 94°–95° C., (88.0%). IR (liquid film): 3370, 3080, 3000, 2930, 2900, 2860, 1725, 1630, 1605, 1595, 860, 840, 780 cm,$^{-1}$ Mass (m/e) EI: 455 (M+).

B. Alpha-oximoketone (21)

Intermediate 20 (1.0 g, 2.2 mmol), isoamyl nitrite (0.4 ml, 3.06 mmol), and potassium t-butoxide (0.60 g, 5.31 mmol) in t-butanol (25 ml) were heated in a water bath with stirring for 40 min. Water was then added and the mixture was adjusted to pH 7 with acetic acid (0.3 ml). This mixture was extracted (ether) six times and the organic layer was washed with brine. The combined organic layers were dried and the solvent removed to give 0.55 g (68%) of α-oximinoketone 21, mp 220°–223° C., CIMS 371 (M+ +1).

C. Benzopyrazine (16)

A mixture of α-oximinoketone 21 (0.16 g, 0.39 mmol) and 1,2-phenylenediamine (0.042 g, 0.39 mmol) was dissolved in dimethyl formamide (DMF) (1 ml) and stirred for 19 hr at 100° C. The DMF was removed in vacuo and to the solid residue were added methanol, saturated aqueous sodium bicarbonate and chloroform. This mixture was stirred, filtered and extracted with chloroform (3 times). The extract was washed with brine, dried and the solvent removed to give brown oil which was purified by column chromatography (Sephadex TM —MeOH) to afford 40 mg (22%) of the pure pyrazine (16). FABMS m/e +VE 428 (M+ +1). IR (liquid film): 3460, 3350, 3020, 2920, 2825, 1637, 1620 cm$^{-1}$.

EXAMPLE VI 17-cyclopropylmethyl-6,7-dehydro-4,5α-epoxy-3,14-dihydroxy-6,7,2',3'-quinolinomorphinan (17)

To a solution of naltrexone.HCl (200 mg, 0.52 mmol) in ethanol (5 ml) were added 2-aminobenzaldehyde (180 mg, 1.50 mmol) and methanesulfonic acid (0.07 ml 0.73 mmol). The mixture was stirred under reflux for 14 hr. Ethyl acetate (EtOAc) and saturated sodium bicarbonate solution were added to the mixture. The mixture was filtered and the filtrate was extracted three times with EtOAc. The combined organic phases were washed with brine, dried, and concentrated to give a crude product. Methanol was added to the product to afford a precipitate which was collected and washed with MeOH to give pure 17 (200 mg, 88.6%), mp. 168°–170° C.; Rf, 0.28 (CHCl$_3$—MeOH—NH$_4$OH, 19/1/0.1); IR (KBr, cm$^{-1}$): 2918, 2825, 1637, 1616 EIMS: 426 (M+).

The physical properties of compounds 1–17 are summarized in Table III.

TABLE III

Physical Properties of 6,7-Dehydro-3,14-dehydroxy-4,5α-epoxymorphinans

| Compound No. | Solvent/Acid Used in Synthesis | MS[a] | R$_f$[b] | Yield (%) |
| --- | --- | --- | --- | --- |
| 1 | MeOH.HCl[f] | 414 | 0.43 | 71 |
| 2 | CH$_3$CO$_2$H | 428 | 0.79 | 70 |
| 3 | CH$_3$CO$_2$H | 432[c] | 0.37 | 56 |
| 4 | CH$_3$CO$_2$H | 444 | 0.39 | 56 |
| 5 | CH$_3$CO$_2$H—HCl[g] | 428 | 0.52 | 70 |
| 6 | CH$_3$CO$_2$H—HCl[g] | 459 | 0.42 | 55 |
| 7 | MeOH.HCl | 374 | 0.13 | 60 |
| 8 | EtOH—CH$_3$SO$_3$H | 415 | 0.70[d] | 80 |
| 9[h] | BBr$_3$ | 430 | 0.16 | 25 |
| 10 | MeOH.HCl | 432 | 0.36 | 80 |
| 11 | MeOH.HCl | 432 | 0.34 | 50 |
| 12 | MeOH.HCl | 428 | 0.50 | 55 |
| 13 | MeOH.HCl | 428 | 0.52 | 55 |
| 14 | MeOH.HCl | 444 | 0.47 | 40 |
| 15 | MeOH.HCl | 430[e] | 0.12 | 20 |
| 16 | DMF | 428[e] | 0.27[i] | 22 |
| 17 | EtOH—CH$_3$SO$_3$H | 426 | 0.28[i] | 88 |

[a]The molecular ion (M+) in the EIMS unless otherwise specified.
[b]Unless otherwise specified, TLC was performed on silica gel GF (0.25 mm) using 10:90:0.2 ratio of MeOH/CHCl$_3$/NH$_4$OH.
[c]CIMS.
[d]Solvent system, Butanol/acetone/water (2:1:1).
[e]FABMS (M+ + 1).
[f]Dry HCl gas was bubbled through 50 ml of MeOH for 10 min.
[g]Ratio 4:1.
[h]Derived from 4 using 5 equivalents of BBr$_3$.
[i]MeOH/CHCl$_3$/NH$_4$OH (1:19:0.1)

EVALUATION OF ANTAGONIST ACTIVITY

A. Materials and Methods

1. Guinea Pig Ileal Longitudinal Muscle (GPI). Ilea from guinea pigs were taken approximately 10 cm from the ileocaecal junction, and a strip of longitudinal muscle with the myenteric plexus attached was prepared by method of Rang et al., *Brit. J. Pharmacol.*, 22, 356 (1964), the disclosure of which is incorporated by reference herein. A 1 cm portion of this strip was then mounted between two platinum electrodes placed in a 10 ml organ bath and connected to an isometric transducer; contractions were recorded on a polygraph. Contractions of the ileal strip were initiated by supramaximal rectangular pulses in all preparations (80 V of 0.5 ms duration at a frequency of 0.1 Hz). Krebs bicarbonate solution containing 1.25 μM chlorpheniramine maleate was the bathing solution and was continuously bubbled with 95% $O_2$ and 5% $CO_2$. The organ bath was maintained at 36°-37° C. The longitudinal muscle strip was allowed to equilibrate with continuous stimulation for a minimum of 90 min. Cumulative concentration-response curves were determined after drugs were added to the bath in 10- to 50-μL amounts and washed out with two 10 ml portions of buffer after noting their maximum effects.

2. Mouse Vas Deferens (MVD)

This assay was performed according to the description by Henderson et al., Brit. J. Pharmacol., 46, 764 (1972), the disclosure of which is incorporated by reference herein. Both vasa deferentia were dissected out of mice and mounted singly through two platinum ring electrodes in a 10 ml organ bath. The bath contained Krebs bicarbonate solution that was continuously bubbled with 95% $O_2$ and 5% $CO_2$. The organ bath was maintained at 37° C. The tissue was attached to an isometric transducer and stimulated transmurally with rectangular pulses (0.1 Mz, 1 ms duration, supramaximal voltage). Drugs were added cumulatively to the bath in 10- to 50-μl amounts and washed out after noting their maximum effect.

B. Pharmacology

The compounds were tested in vitro on the mouse vas deferens (MVD) and guinea pig ileum (GPI) preparations. Each compound (100 or 200 nM) was incubated for 15 min with the tissue prior to adding graded doses of a standard agonist for determination of an $IC_{50}$ value. The standard agonists employed were [D-Ala$^2$, D-Leu$^5$-]enkephalin (DADLE), morphine (M), and ethylketazocine (EK); these are selective for delta, mu, and kappa opioid receptors, respectively. The $IC_{50}$ value was divided by the control $IC_{50}$ value in the same tissue, and this $IC_{50}$ ratio (DR) was employed to calculate the Ke value using the equation $Ke=[antagonist]/(DR-1)$. The results of these bioassays are summarized on Table IV, below.

TABLE IV

In Vitro Antagonist Activity of 6,7-Dehydro-3,14-dihydroxy-4,5α-epoxymorphinan Derivatives

| Compound No. | Ke (nM)$^a$ | | |
|---|---|---|---|
| | DADLE$^b$ | M$^c$ | EK$^d$ |
| 1 | 0.22 | 29.4 | 45.5 |
| 2 | 1.5 | 12.5 | 22.2 |
| 3 | 2.0 | 61.7 | 46.2 |
| 4 | 5.7 | 63.0 | 12.6 |
| 5 | 4.2 | >160 | >250 |
| 6 | 168.0 | 92.0 | ≧200 |
| 7 | e | e | e |
| 8 | 1.8 | 30.8 | 50.8 |
| 9 | — | 27.2 | 68.5 |
| 10 | 5.5 | >125 | >170 |
| 11 | 0.35 | 5.3 | >330 |
| 12 | 4.8 | >125 | >143 |
| 13 | 1.5 | 19.1 | >330 |
| 14 | 6.6 | 35 | — |
| 16 | 1.4 | 6.1 | 13.4 |

TABLE IV-continued

In Vitro Antagonist Activity of 6,7-Dehydro-3,14-dihydroxy-4,5α-epoxymorphinan Derivatives

| Compound No. | Ke (nM)$^a$ | | |
|---|---|---|---|
| | DADLE$^b$ | M$^c$ | EK$^d$ |
| 17 | 2.7 | 11.3 | 16.3 |

$^a$Ke = [antagonist]/($IC_{50}$ ratio-1), where the $IC_{50}$ ratio represents the response of the tissue to an agonist in the presence of the antagonist divided by the control $IC_{50}$ of the agonist in the same tissue.
$^b$[D-ala$^2$, D-Leu$^5$] enkephalin in the mouse vas deferens preparation (MVD).
$^c$Morphine in the guinea pig ileum preparation (GPI).
$^d$Ethylketazocine in the GPI.
$^e$No agonist antagonism observed.

All of the N-cyclopropylmethyl compounds (1-6, 8-14 and 16-17 antagonized the effect of the delta agonist, DADLE. Substantially less antagonism toward morphine and EK was observed. These compounds were devoid of agonist activity or behaved as weak, partial agonists, with dose-response curves that plateaued at 20-40% of the maximal response at a concentration of 1 μM. The agonist effect was consistently below 20% at the concentrations employed (20-200 nM) for antagonist testing.

The N-methyl compound 7 also exhibited partial agonist activity. However, because its agonist effect was below 20% only at 5 nM or less, it was tested for antagonist activity at this concentration and was found to be inactive in this regard.

The highly active delta antagonist 1 of the series was evaluated in mice for its effectiveness in antagonizing the antinociceptive effect of Tyr-D-Ser-Gly-Phe-Leu-Thr (DSLET), morphine, and U50488H. These agonists were employed because their agonism is selectively mediated through delta, mu and kappa opioid receptors, respectively.

TABLE V

| In Vivo Antagonist Activity of NTI (1) in Mice* | |
|---|---|
| Agonist | $ED_{50}$ Ratio$^a$ |
| DSLET$^b$ | 5.25 (2.70-11.11) |
| Morphine$^c$ | 1.15 (0.54-2.78) |
| U50488H$^c$ | 1.23 (0.63-2.86) |

*Methodology of G. Hayashi et al., Eur. J. Pharmacol., 16, 63 (1971).
$^a$$ED_{50}$ value of treated mice (20 mg/kg SC) divided by $ED_{50}$ of control mice.
$^b$Administered intracerebroventicularly (ICV).
$^c$Administered subcutaneously (SC).

Compound 1 at 20 mg/kg s.c. effectively blocked the writhing inhibition due to DSLET ($ED_{50}$ ratio=5) without significantly antagonizing the effect of morphine or U50488H.

DISCUSSION

Both the in vitro and in vivo data show that fusion of the indole, benzofuran, benzopyrazine or quinoline ring system to the C-ring of naltrexone gives rise to compounds that possess a unique opioid receptor antagonist profile. Most of these compounds are highly selective for the delta opioid receptor, and the unsubstituted indole 1 appears to be an order of magnitude more potent than its substituted congeners. The selectivity ratios of NTI are approximately 50 for delta/mu, and possibly greater for delta/kappa.

Judging from the decreased potency upon substitution of the indole benzene ring by either electron donating or withdrawing groups, it appears that the predominant factors contributing to the observed selectivity are of steric origin. In this regard, it is apparent that reduction of antagonist potency also was effected with methyl substitution on the pyrrole nitrogen (e.g., compound 2).

It can be noted that the benzofuran 8, while less potent and less selective than 1 as a delta antagonist, nevertheless retains substantial delta antagonist activity. A similar relationship was observed with the benzopyrazine 16 and the quinoline 17. This indicates that the indole ring system is not necessary for delta selectivity. Possibly, the role of the pyrrole, furan, pyrazine and quinoline moieties in these compounds is to restrain the additional benzene ring so that it is a coplanar to the C-ring of the morphinan nucleus.

The fact that the oxymorphone-indole adduct 7 was substantially more potent as an agonist than the N-cyclopropyl analogues is not surprising in view of the well-known ability of the latter group to confer opioid antagonism. There could be an antagonist component associated with the action of 7, but this may be masked by the agonist effect.

In conclusion, 1 is the first nonpeptide that is a highly selective delta opioid receptor antagonist. In fact, it is considerably more potent than the peptide delta antagonist, ICI 174864 and far more selective than the opiate M8008 [Ke (nM)=0.73, See C. F. C. Smith, Life Sci., 40, 267 (1987)]. The high selectivity and opiate potency of 1 make this compound a potentially valuable tool in opioid research. This is particularly true for in vivo studies where the blood-brain barrier is an obstacle to penetration by ICI 174864. Additionally, 1 may find application in clinical cases where selective blockage of delta opioid receptors is desirable.

The invention has been described with reference to various specific and preferred embodiments and techniques. However, it should be understood that many variations and modifications may be made while remaining within the spirit and scope of the invention.

What is claimed is:

1. A compound of the formula:

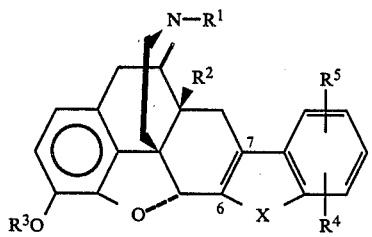

wherein $R^1$ is $(C_1-C_5)$alkyl, $C_3-C_6$(cycloalkyl)alkyl, $C_5-C_7$(cycloalkenyl)alkyl, aryl, aralkyl, trans($C_4-C_5$)alkenyl, allyl or furan-2-ylalkyl, $R^2$ is H, OH or $O_2C(-C_1-C_5)$alkyl; $R^3$ is H or $((C_1-C_5)$alkyl$)C=O$; X is O, S or NY, wherein Y is H or $(C_1-C_5)$alkyl; and $R^4$ and $R^5$ are individually H, F, Cl, Br, $NH_2$, $NO_2$, $(C_1-C_5)$alkyl or $(C_1-C_5)$alkoxy or $R^4$ and $R^5$ together are benzo; and the pharmaceutically acceptable salts thereof.

2. The compound of claim 1 wherein $R^1$ is $C_3-C_6$(cycloalkyl)alkyl or $(C_1-C_5)$alkyl.

3. The compound of claim 2 wherein $R^1$ is cyclopropylmethyl or methyl.

4. The compound of claim 1 wherein $R^1$ is cyclopropylmethyl.

5. The compound of claim 1 wherein $R^2$ is OH or $OC=O(C_1-C_5)$alkyl.

6. The compound of claim 1 wherein $R^3$ is H.

7. The compound of claim 1 wherein X is NH or O.

8. The compound of claim 1 wherein $R^4$ is F.

9. The compound of claim 1 wherein $R^5$ is H.

10. The compound of claim 1 wherein $R^4$ is H and $R^5$ is H.

11. The compound of claim 1 wherein $R^4$ is H and $R^5$ is $CH_3$.

12. The compound of claim 1 wherein $R^4$ is OH or $OCH_3$.

13. The compound of claim 1 wherein $R^4$ and $R^5$ together are benzo.

14. A compound of the formula:

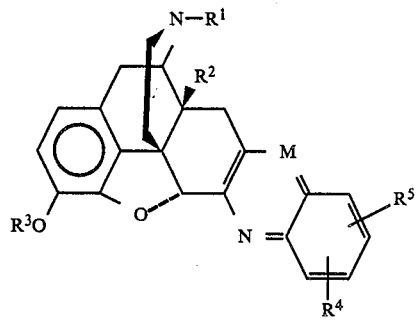

wherein $R^1$ is $(C_1-C_5)$alkyl, $C_3-C_6$(cycloalkyl)alkyl, $C_5-C_7$(cycloalkenyl)alkyl, aryl, aralkyl, trans($C_4-C_5$)alkenyl, allyl or furan-2-ylalkyl, $R^2$ is H, OH or $O_2C(-C_1-C_5)$alkyl; $R^3$ is H or $((C_1-C_5)$alkyl$)C=O$; M is N or CH and $R^4$ and $R^5$ are individually H, F, Cl, Br, $NO_2$, $NH_2$, $(C_1-C_5)$alkyl or $(C_1-C_5)$alkoxy or $R^4$ and $R^5$ together are benzo; and the pharmaceutically acceptable salts thereof.

15. The compound of claim 14 wherein $R^1$ is $C_3-C_6$(cycloalkyl)alkyl or $(C_1-C_5)$alkyl.

16. The compound of claim 15 wherein $R^1$ is cyclopropylmethyl or methyl.

17. The compound of claim 14 wherein $R^1$ is cyclopropylmethyl.

18. The compound of claim 14 wherein $R^2$ is OH or $O_2C(C_1-C_5)$alkyl.

19. The compound of claim 14 wherein $R^3$ is H or $((C_1-C_5)$alkyl$)C=O$.

20. The compound of claim 14 wherein $R^3$ is H.

21. The compound of claim 14 wherein $R^4$ is H.

22. The compound of claim 21 wherein $R^5$ is H.

23. The compound of claim 14 wherein M is N.

24. The compound of claim 14 wherein M is CH.

25. The compound of claim 14 wherein $R^4$ and $R^5$ together are benzo.

* * * * *

UNITED STATES PATENT AND TRADEMARK OFFICE
CERTIFICATE OF CORRECTION

PATENT NO. : 4,816,586
DATED : March 28, 1989
INVENTOR(S) : Philip S. Portoghese It is certified that error appears in the above-identified patent and that said Letters Patent is hereby corrected as shown below:

At Col. 2, line 12, for "$C_3 14\ C_6$" read --$C_3$-$C_6$--.

At Col. 2, line 13, for "$C_5 14\ C_7$" read --$C_5$-$C_7$--.

At Col. 2, formula II, for "N" read --M--. (Copy marked.)

At Col. 4, line 59, for "$C_5 14\ C_7$" read --$C_5$-$C_7$--.

Signed and Sealed this

Sixteenth Day of January, 1990

*Attest:*

JEFFREY M. SAMUELS

*Attesting Officer*   Acting Commissioner of Patents and Trademarks

UNITED STATES PATENT AND TRADEMARK OFFICE
CERTIFICATE OF CORRECTION

PATENT NO. : 4,816,586

DATED : March 28, 1989

INVENTOR(S) : Portoghese

It is certified that error appears in the above-identified patent and that said Letters Patent is hereby corrected as shown below:

In Column 3, Table I, delete the chemical graphic that reads

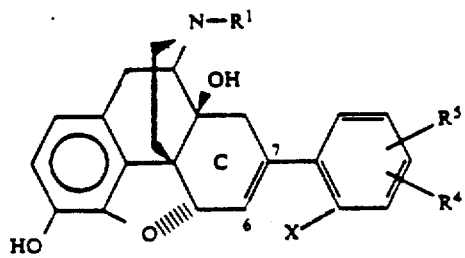

and insert therefore

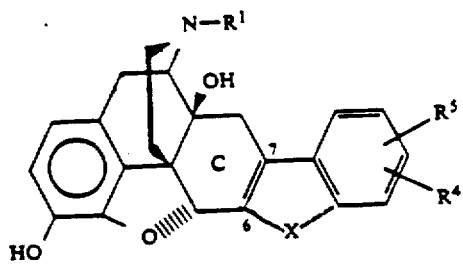

UNITED STATES PATENT AND TRADEMARK OFFICE
CERTIFICATE OF CORRECTION

PATENT NO. : 4,816,586
DATED : March 28, 1989
INVENTOR(S) : Portoghese

It is certified that error appears in the above-indentified patent and that said Letters Patent is hereby corrected as shown below:

In Column 4, Table I, delete the chemical graphic that reads

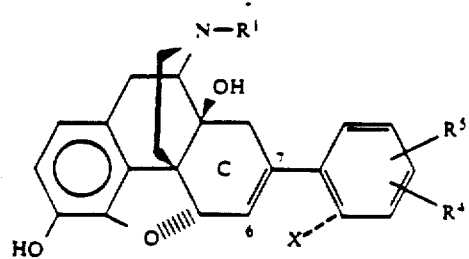

UNITED STATES PATENT AND TRADEMARK OFFICE
CERTIFICATE OF CORRECTION

PATENT NO. : 4,816,586
DATED : March 28, 1989
INVENTOR(S) : Portoghese

Page 3 of 3

It is certified that error appears in the above-indentified patent and that said Letters Patent is hereby corrected as shown below:

and insert therefore

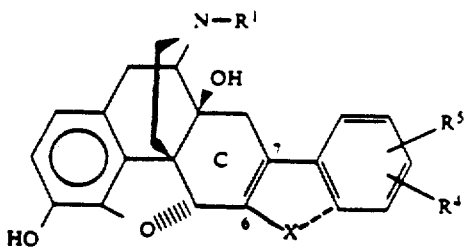

Signed and Sealed this

Eighth Day of March, 1994

Attest:

*Attesting Officer*

BRUCE LEHMAN
*Commissioner of Patents and Trademarks*